United States Patent
Sharma et al.

(10) Patent No.: US 6,576,581 B1
(45) Date of Patent: Jun. 10, 2003

(54) AROMATICS ISOMERIZATION USING A DUAL-CATALYST SYSTEM

(75) Inventors: Sanjay B. Sharma, Burr Ridge, IL (US); Aaron J. Imrie, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 35 days.

(21) Appl. No.: 09/746,584

(22) Filed: Dec. 21, 2000

Related U.S. Application Data

(62) Division of application No. 09/348,119, filed on Jul. 2, 1999, now Pat. No. 6,222,086.

(51) Int. Cl.$^7$ .......................... B01J 29/068; B01J 29/44; B01J 29/85
(52) U.S. Cl. .................... 502/66; 502/64; 502/67; 502/71; 502/74; 502/77; 502/213; 502/214
(58) Field of Search ........................ 502/60, 64, 66, 502/71, 67, 74, 77, 208, 213, 214

(56) References Cited

U.S. PATENT DOCUMENTS

| | | | | |
|---|---|---|---|---|
| 3,856,872 A | | 12/1974 | Morrison ................ | 260/668 A |
| 4,351,979 A | * | 9/1982 | Chester et al. ................ | 208/66 |
| 4,740,650 A | | 4/1988 | Pellet et al. ................ | 585/480 |
| 4,818,739 A | * | 4/1989 | Gortsema et al. ........... | 502/208 |
| 4,899,011 A | | 2/1990 | Chu et al. .................... | 585/481 |
| 5,149,421 A | * | 9/1992 | Miller ..................... | 208/111.2 |
| 5,240,891 A | | 8/1993 | Patton et al. ................. | 502/66 |
| 5,612,273 A | * | 3/1997 | Prada et al. ................ | 502/313 |
| 5,770,542 A | * | 6/1998 | Brandes et al. ............... | 502/67 |
| 5,833,837 A | * | 11/1998 | Miller ........................ | 208/114 |
| 5,898,090 A | | 4/1999 | Hammerman et al. ...... | 885/477 |
| 6,222,086 B1 | * | 4/2001 | Sharma et al. .............. | 585/481 |

\* cited by examiner

*Primary Examiner*—Tom Dunn
*Assistant Examiner*—Christina Ildebrando
(74) *Attorney, Agent, or Firm*—John G. Tolomei; Frank S. Molinaro; Thomas K. McBride, Jr.

(57) ABSTRACT

This invention is drawn to a catalyst system comprising two or more molecular sieves, including at least one non-zeolitic molecular sieve and one zeolitic aluminosilicate, having specified contrasting pore structures and to a process for isomerizing a non-equilibrium mixture of xylenes and ethylbenzene using the subject catalyst system to obtain an improved yield of para-xylene from the mixture relative to prior-art processes.

10 Claims, 1 Drawing Sheet

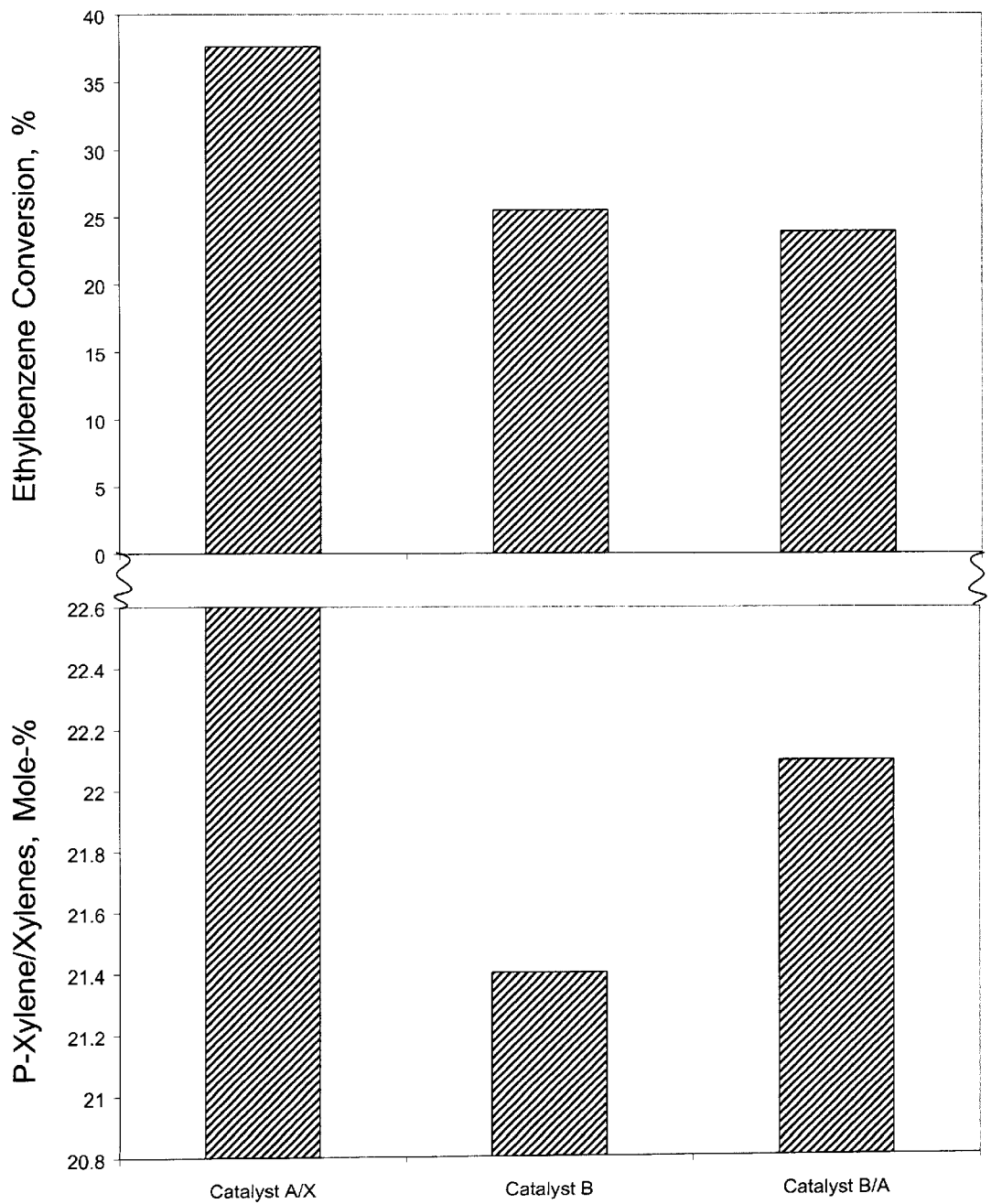

AROMATICS ISOMERIZATION USING A DUAL-CATALYST SYSTEM

CROSS REFERENCE TO RELATED APPLICATION

This application is a divisional application of Ser. No. 09/348,119 filed Jul. 2, 1999, now U.S. Pat. No. 6,222,086, the contents of which are incorporated by reference thereto.

FIELD OF THE INVENTION

This invention relates to catalytic hydrocarbon conversion, and more specifically to the use of an improved molecular-sieve catalyst system in aromatics isomerization.

GENERAL BACKGROUND AND RELATED ART

The xylenes, para-xylene, meta-xylene and ortho-xylene, are important intermediates which find wide and varied application in chemical syntheses. Para-xylene upon oxidation yields terephthalic acid which is used in the manufacture of synthetic textile fibers and resins. Meta-xylene is used in the manufacture of plasticizers, azo dyes, wood preservers, etc. Ortho-xylene is feedstock for phthalic anhydride production.

Xylene isomers from catalytic reforming or other sources generally do not match demand proportions as chemical intermediates, and further comprise ethylbenzene which is difficult to separate or to convert. Paraxylene in particular is a major chemical intermediate with rapidly growing demand, but amounts to only 20-25% of a typical $C_8$ aromatics stream. Adjustment of isomer ratio to demand can be effected by combining xylene-isomer recovery, such as adsorption for para-xylene recovery, with isomerization to yield an additional quantity of the desired isomer. Isomerization converts a non-equilibrium mixture of the xylene isomers which is lean in the desired xylene isomer to a mixture approaching equilibrium concentrations.

Various catalysts and processes have been developed to effect xylene isomerization. In selecting appropriate technology, it is desirable to run the isomerization process as close to equilibrium as practical in order to maximize the para-xylene yield; however, associated with this is a greater cyclic $C_8$ loss due to side reactions. The approach to equilibrium that is used is an optimized compromise between high $C_8$ cyclic loss at high conversion (i.e. very close approach to equilibrium) and high utility costs due to the large recycle rate of unconverted $C_8$ aromatics. Catalysts thus are evaluated on the basis of a favorable balance of activity, selectivity and stability Catalysts containing molecular sieves have become prominent for xylene isomerization in the past quarter-century or so. U.S. Pat. No. 3,856,872 (Morrison), for example, teaches xylene isomerization and ethylbenzene conversion with a catalyst containing ZSM-5, -12, or -21 zeolite U.S. Pat. No. 4,740,650 (Pellet et al.) teaches xylene isomerization using a catalyst containing at least one non-zeolitic molecular sieve which preferably is a silicoaluminophosphate. U.S. Pat. No. 4,899,011 teaches isomerization of $C_8$ aromatics using two zeolites, each of which is associated with a strong hydrogenation metal. U.S. Pat. No. 5,240,891 (Patton et al.) discloses a MgAPSO molecular sieve having a narrow ratio of framework magnesium and its use in xylene isomerization. U.S. Pat. No. 5,898,090 (Hammerman et al.) teaches isomerization of a mixture of xylenes and ethylbenzene using an SM-3 silicoaluminophosphate molecular sieve. Although these references teach individual elements of the present invention, none of the art suggests combination of the elements to obtain the critical features of the catalyst system and its use of the present invention.

Catalysts for isomerization of $C_8$ aromatics ordinarily are classified by the manner of processing ethylbenzene associated with the xylene isomers. Ethylbenzene is not easily isomerized to xylenes, but it normally is converted in the isomerization unit because separation from the xylenes by superfractionation or adsorption is very expensive. A widely used approach is to dealkylate ethylbenzene to form principally benzene while isomerizing xylenes to a near-equilibrium mixture. An alternative approach is to react the ethylbenzene to form a xylene mixture via conversion to and reconversion from naphthenes in the presence of a solid acid catalyst with a hydrogenation-dehydrogenation function. The former approach commonly results in higher ethylbenzene conversion and more effective xylene isomerization, thus lowering the quantity of recycle in a loop of isomerization/para-xylene recovery and reducing concomitant processing costs, but the latter approach enhances xylene yield by forming xylenes from ethylbenzene. A catalyst system and process which combines the features of the approaches, i.e., achieves ethylbenzene isomerization to xylenes with high conversion of both ethylbenzene and xylenes, would effect significant improvements in xylene-production economics.

SUMMARY OF THE INVENTION

A principal object of the present invention is to provide a novel catalyst and process for the isomerization of alkylaromatic hydrocarbons. More specifically, this invention is directed to a catalyst system for isomerization of $C_8$ aromatic hydrocarbons to obtain improved yields of desired xylene isomers.

This invention is based on the discovery that a catalyst system comprising a combination of a non-zeolitic molecular-sieve catalyst and a zeolitic aluminosilicate catalyst having critically defined characteristics demonstrates improved conversion and selectivity in $C_8$ aromatics isomerization.

Accordingly, a broad embodiment of the invention is directed toward a catalyst system useful for the isomerization of alkylaromatics comprising a combination of a first catalyst comprising a non-zeolitic molecular sieve and a platinum-group metal and a second catalyst comprising a zeolitic aluminosilicate and a platinum-group metal in a substantially lower concentration than in the first catalyst. The non-zeolitic molecular sieve preferably is a silicoaluminophosphate (SAPO) molecular-sieve, more preferably an SM-3 and/or a MgAPSO molecular sieve which preferably comprises a MgAPSO-31 molecular sieve. Platinum is the preferred platinum-group metal, and is in a concentration on the second catalyst of no more than about 30% of the concentration on the first catalyst; preferably, this relative concentration is no more than about 20%, and optionally no more than about 10% of platinum on the second catalyst relative to platinum on the first catalyst. The optimal catalysts generally comprise an inorganic-oxide binder, usually alumina and/or silica.

In one embodiment, the non-zeolitic molecular sieve and the zeolitic aluminosilicate are staged, preferably with a bed of the non-zeolitic molecular sieve preceding a bed of the zeolitic aluminosilicate. In another aspect of the invention, the non-zeolitic molecular sieve and zeolitic aluminosilicate are contained on separate particles which comprise a physical mixture.

A further embodiment of the invention is an alkylaromatics-isomerization process, stock using a catalyst system comprising a combination of a first catalyst comprising a non-zeolitic molecular sieve and a platinum-group metal and a second catalyst comprising a zeolitic aluminosilicate and a platinum-group metal in a substantially lower concentration than in the first catalyst to isomerize a feed mixture to obtain an isomerized product. Preferably the isomerization is effected by the steps of contacting the feed mixture with a non-zeolitic molecular-sieve catalyst to obtain an isomerized intermediate which then is contacted with a zeolitic aluminosilicate to increase the proportion of at least one xylene isomer in an isomerized product. Preferably the process comprises isomerization of a feedstock comprising a non-equilibrium mixture of xylenes and ethylbenzene at isomerization conditions to obtain a product having an increased para-xylene content relative to that of the feed.

These as well as other objects and embodiments will become evident from the following detailed description of the invention.

BRIEF DESCRIPTION OF THE DRAWING

The FIGURE shows ethylbenzene conversion and product paraxylene/xylenes ratio when using the catalyst system of the invention in comparison to the known art.

DETAILED DESCRIPTION OF THE INVENTION

The feedstock to aromatics isomerization comprises isomerizable alkylaromatic hydrocarbons of the general formula $C_6H_{(6-n)}R_n$, where n is an integer from 2 to 5 and R is $CH_3$, $C_2H_5$, $C_3H_7$, or $C_4H_9$, in any combination and including al the isomers thereof to obtain more valuable isomers of the alkylaromatic. Suitable alkylaromatic hydrocarbons include, for example but without so limiting the invention, ortho-xylene, meta-xylene, para-xylene, ethylbenzene, ethyltoluenes, tri-methylbenzenes, di-ethylbenzenes, tri-ethyl-benzenes, methylpropylbenzenes, ethylpropylbenzenes, di-isopropylbenzenes, and mixtures thereof.

Isomerization of a $C_8$ aromatic mixture containing ethylbenzene and xylenes is a particularly preferred application of the catalyst system of the invention. Generally such mixture will have an ethylbenzene content in the approximate range of 1 to 50 mass-%, an ortho-xylene content in the approximate range of 0 to 35 mass-%, a meta-xylene content in the approximate range of 20 to 95 mass-% and a para-xylene content in the approximate range of 0 to 30 mass-%. It is preferred that the aforementioned $C_8$ aromatics comprise a non-equilibrium mixture, i.e., at least one $C_8$ aromatic isomer is present in a concentration that differs substantially from the equilibrium concentration at isomerization conditions.

Usually the non-equilibrium mixture is prepared by removal of para-, ortho- and/or meta-xylene from a fresh $C_8$ aromatic mixture obtained from an aromatics-production process.

The alkylaromatic hydrocarbons may be utilized in the present invention as found in appropriate fractions from various refinery petroleum streams, e.g., as individual components or as. certain boiling-range fractions obtained by the selective fractionation and distillation of catalytically cracked or reformed hydrocarbons. The isomerizable aromatic hydrocarbons need not be concentrated; the process of this invention allows the isomerization of alkylaromatic-containing streams such as catalytic reformate with or without subsequent aromatics extraction to produce specified xylene isomers and particularly to produce para-xylene. A C8 aromatics feed to the present process may contain nonaromatic hydrocarbons, i.e., naphthenes and paraffins, in an amount up to 30 mass-%. Preferably the isomerizable hydrocarbons consist essentially of aromatics, however, to ensure pure products from downstream recovery processes.

According to the process of the present invention, an alkylaromatic hydrocarbon feed mixture, preferably in admixture with hydrogen, is contacted with two or more catalysts of the type hereinafter described in an alkylaromatic-hydrocarbon isomerization zone. Contacting may be effected using the catalyst system in a fixed-bed system, a moving-bed system, a fluidized-bed system, slurry system or ebullated-bed system or in a batch-type operation. In view of the danger of attrition loss of valuable catalysts and of the simpler operation, it is preferred to use a fixed-bed system. In this system, a hydrogen-rich gas and the feed mixture are preheated by suitable heating means to the desired reaction temperature and then passed into an isomerization zone containing a fixed bed or beds of two or more catalysts. The conversion zone may be one or more separate reactors with suitable means therebetween to ensure that the desired isomerization temperature is maintained at the entrance to each zone. The reactants may be contacted with the catalyst bed in either upward-, downward-, or radial-flow fashion, and the reactants may be in the liquid phase, a mixed liquid-vapor phase, or a vapor phase when contacted with the catalyst.

Catalysts containing the more non-zeolitic molecular-sieves and zeolitic aluminosilicate may be contained in separate reactors, arranged sequentially in the same reactor, mixed physically, or composited as a single catalyst. Preferably the catalysts are arranged in sequence, with the feed first contacting the non-zeolitic molecular-sieve catalyst to obtain an isomerized intermediate which then contacts the zeolitic-aluminosilicate catalyst to yield the isomerized product. The catalyst system preferably consists essentially of the sequence of non-zeolitic molecular-sieve and zeolitic-aluminosilicate catalysts. Alternatively, the feed may contact the zeolitic-aluminosilicate catalyst prior to the non-zeolitic molecular-sieve catalyst.

Location of the catalysts in separate reactors would permit independent control of operating conditions, particularly temperature and space velocity. By employing a single reactor, however, savings are realized in piping, instrumentation and other appurtenances. Physical mixing of the catalysts would facilitate synergistic reactions of the catalysts, but separation and recovery of catalyst components would be more difficult. The system of catalysts optionally may be repeated in one or more additional stages, i.e., reactants from the contacting of the feed are processed in another sequence of the two catalysts.

In an alternative embodiment of the invention, therefore, the reactor contains a physical mixture of individual catalysts containing the non-zeolitic molecular sieve and the zeolitic aluminosilicate. In this embodiment, particles are mechanically mixed to provide the catalyst system of the invention. The particles can be thoroughly mixed using known techniques such as mulling to intimately blend the physical mixture. Although the first and second particles may be of similar size and shape, the particles preferably are of different size and/or density for ease of separation for purposes of regeneration or rejuvenation following their use in hydrocarbon processing.

As yet another alternative embodiment of the present invention, a physical mixture of non-zeolitic molecular sieves and zeolitic aluminosilicate is contained within the same catalyst particle. In this embodiment, the sieves may be ground or milled together or separately to form particles of suitable size, preferably less than 100 microns, and the particles are supported in a suitable matrix. Optimally the matrix is selected from the inorganic oxides described hereinabove. As a variant of this embodiment, the NZMSs are as a multi-compositional, multi-phase composite having contiguous phases, especially wherein one phase comprises a deposition substrate upon which another phase is deposited as an outer layer. Such composites are described in U.S. Pat. No. 4,861,739, incorporated herein by reference thereto.

The alkylaromatic feed mixture, preferably a non-equilibrium mixture of $C_8$ aromatics, is contacted with the isomerization catalysts at suitable alkylaromatic-isomerization. conditions. Such conditions comprise a temperature ranging from about 100° to 600° C. or more, and preferably in the range of from about 300° to 500° C. The pressure generally is from about 100 kPa to 5 MPa absolute, preferably less than about 3 MPa. A sufficient volume of both catalysts comprising the catalyst system is contained in the isomerization zone to provide a liquid hourly space velocity with respect to the hydrocarbon feed mixture of from about 0.5 to 50 $hr^{-1}$, and preferably 0.5 to 20 $hr^{-1}$; with respect to each of the catalysts comprising the catalyst system, the space velocity is within the range of about 1 to 100 $hr^{-1}$. The hydrocarbon feed mixture optimally is reacted in admixture with hydrogen at a hydrogen/hydrocarbon mole ratio of about 0.5:1 to 25:1. Other inert diluents such as nitrogen, argon and light hydrocarbons may be present. If the two or more catalysts are contained in separate beds, different operating conditions within the above constraints may be used within each of the beds in order to achieve optimum overall results.

The particular scheme employed to recover an isomerized product from the effluent of the reactors of the isomerization zone is not deemed to be critical to the instant invention, and any effective recovery scheme known in the art may be used. Typically, the reactor effluent will be condensed and the hydrogen and light-hydrocarbon components removed therefrom by flash separation. The condensed liquid product then is fractionated to remove light and/or heavy byproducts and obtain the isomerized product. In some instances, certain product species such as ortho-xylene may be recovered from the isomerized product by selective fractionation. The product from isomerization of $C_8$ aromatics usually is processed to selectively recover the para-xylene isomer, optionally by crystallization. Selective adsorption is preferred using crystalline aluminosilicates according to U.S. Pat. 3,201,491. Improvements and alternatives within the preferred adsorption recovery process are described in U.S. Pat. Nos. 3,626,020, 3,696,107, 4,039,599, 4,184,943, 4,381,419 and 4,402,832, incorporated herein by reference thereto.

In a separation/isomerization process combination relating to the processing of an ethylbenzene/xylene mixture, a fresh $C_8$ aromatic feed is combined with isomerized product comprising $C_8$ aromatics and naphthenes from the isomerization reaction zone and fed to a para-xylene separation zone; the para-xylene-depleted stream comprising a non-equilibrium mixture of $C_8$ aromatics is fed to the isomerization reaction zone, where the $C_8$ aromatic isomers are isomerized to near-equilibrium levels to obtain the isomerized product. In this process scheme non-recovered $C_8$ aromatic isomers preferably are recycled to extinction until they are either converted to para-xylene or lost due to side-reactions. Ortho-xylene separation, preferably by fractionation, also may be effected on the fresh $C_8$ aromatic feed or isomerized product, or both in combination, prior to para-xylene separation.

As noted hereinabove, the present invention is drawn to a catalyst system and its use in isomerization of $C_8$ aromatics comprising a non-zeolitic molecular-sieve first catalyst and a zeolitic aluminosilicate second catalyst having differing contents of platinum-group metal components. The mass ratio of first catalyst to second catalyst depends primarily on the feedstock composition and desired product distribution, with a first:second catalyst mass ratio of from about 1:20 to 50:1being preferred and from about 1:10 to 20:1 being especially preferred. The catalyst system of the invention may include other catalysts, either sieve-based or amorphous.

An essential component of the first catalyst of the present invention therefore is at least one non-zeolitic molecular sieve, also characterized as "NZMS" and defined in the instant invention to include molecular sieves containing framework tetrahedral units ($TO_2$) of aluminum ($AlO_2$), phosphorus ($PO_2$) and at least one additional element (EL) as a framework tetrahedral unit ($ELO_2$). "NZMS" includes the "SAPO" molecular sieves of U.S. Pat. No. 4,440,871, "ELAPSO" molecular sieves as disclosed in U.S. Pat. No. 4,793,984 and certain "MeAPO", "FAPO", "TAPO" and "MAPO" molecular sieves, as hereinafter described. Crystalline metal aluminophosphates (MeAPOs where "Me" is at least one of Mg, Mn, Co and Zn) are disclosed in U.S. Pat. No. 4,567,029, crystalline ferroaluminophosphates (FAPOs) are disclosed in U.S. Pat. No. 4,554,143, titanium aluminophosphates (TAPOs) are disclosed in U.S. Pat. No. 4,500,651, MAPO metal aluminophosphates wherein M is As, Be, B, Cr, Ga, Ge, Li or V are disclosed in U.S. Pat. No. 4,686,093, and binary metal aluminophosphates are described in Canadian Patent 1,241,943. ELAPSO molecular sieves also are disclosed in patents drawn to species thereof, including but not limited to GaAPSO as disclosed in U.S. Pat. No. 4,735,806, BeAPSO as disclosed in U.S. Pat. No. 4,737,353, CrAPSO as disclosed in U.S. Pat. No. 4,738,837, CoAPSO as disclosed in U.S. Pat. No. 4,744,970, MgAPSO as disclosed in U.S. Pat. No. 4,758,419 and MnAPSO as disclosed in U.S. Pat. No. 4,793,833. The aforementioned patents are incorporated herein by reference thereto. The nomenclature employed herein to refer to the members of the aforementioned NZMSs is consistent with that employed in the aforementioned applications or patents. A particular member of a class is generally referred to as a "-n" species wherein "n" is an integer, e.g., SAPO-11, MeAPO-11 and ELAPSO-31. The preferred elliptical-pore crystalline non-zeolitic molecular sieves are one or more of the AEL framework types, especially SAPO-11, or one or more of the ATO framework types, especially MAPSO-31, according to the *Atlas of Zeolite Structure Types*.

In the following discussion on preferred NZMSs, the mole fractions of the NZMSs are defined as compositional values which are plotted in phase diagrams in each of the identified patents, published applications or copending applications.

The silicoaluminophosphate molecular sieve SAPO-11 described in U.S. Pat. No. 4,440,871, having respective maximum and minimum crystallographic free diameters of 6.3 and 3.9 Å and resulting maximum/minimum ratio of 1.6+, is especially preferred. The silicoaluminophosphate molecular sieves are disclosed as microporous crystalline silicoaluminophosphates, having a three-dimensional microporous framework structure of $PO_2^+$, $AlO_2^-$ and $SiO_2$ tetrahedral units, and whose essential empirical chemical composition on an anhydrous basis is:

$$mR:(Si_xAl_yP_z)O_2$$

wherein "R" represents at least one organic templating agent present in the intracrystalline pore system; "m" represents the moles of "R" present per mole of $(Si_xAl_yP_z)O_2$ and has a value of from 0.02 to 0.3; "x", "y" and "z" represent, respectively, the mole fractions of silicon, aluminum and phosphorus present in the oxide moiety, said mole fractions being within the compositional area bounded by points A, B, C, D and E on the ternary diagram which is FIG. 1 of U.S. Pat. No. 4,440,871, and represent the following values for "x", "y" and "z":

| | Mole Fraction | | |
|---|---|---|---|
| Point | x | y | z |
| A | 0.01 | 0.47 | 0.52 |
| B | 0.94 | 0.01 | 0.05 |
| C | 0.98 | 0.01 | 0.01 |
| D | 0.39 | 0.60 | 0.01 |
| E | 0.01 | 0.60 | 0.39 |

The silicoaluminophosphates of U.S. Pat. No. 4,440,871 are generally referred to therein as "SAPO" as a class, or as "SAPO-n" wherein "n" is an integer denoting a particular SAPO such as SAPO-11, SAPO-31, SAPO-40 and SAPO-41. The especially preferred species SAPO-11 as referred to herein is a silicoaluminophosphate having a characteristic X-ray powder diffraction pattern which contains at least the d-spacings set forth below:

| SAPO-11 | | |
|---|---|---|
| 2Θ | r | Relative Intensity |
| 9.4–9.65 | 9.41–9.17 | m |
| 20.3–20.6 | 4.37–4.31 | m |
| 21.0–21.3 | 4.23–4.17 | vs |
| 21.1–22.35 | 4.02–3.99 | m |
| 22.5–22.9 (doublet) | 3.95–3.92 | m |
| 23.15–23.35 | 3.84–3.81 | ms |

A preferred SAPO-11 for use in the present invention is condensed-silica SAPO-11 denoted as SM-3 and prepared in accordance with the teachings of U.S. Pat. No. 5,158,665 (Miller). SM-3 comprises a $P_2O_5$-to-alumina mole ratio at the surface of the silicoaluminophosphate of about 0.80 or less, preferably from about 0.80 to about 0.55; a $P_2O_5$-to-alumina mole ratio in the bulk of the SAPO of 0.96 or greater, preferably from about 0.96 to 1; and a silica-to-alumina mole ratio at the surface which is greater than in the bulk of the SAPO. Preferably the SM-3 has a composition in terms of mole ratios of oxides on an anhydrous basis of:

$$mR:Al_2O_3:nP_2O_5:qSiO_2$$

wherein "R" represents at least one organic templating agent present in the intracrystalline pore system, "m" represents the moles of "R" present and has a value such that there are from 0.02 to 2 moles of "R" per mole of alumina, n has a value of from 0.96 to 1.1 and preferably 0.96 to 1, and q has a value of from 0.1 to 4 and preferably 0.1 to 1. Miller '424 is incorporated herein by reference for its teachings with respect to preparation and properties of the preferred SM-3.

The alternative preferred crystalline non-zeolitic molecular sieves are one or more of the ATO framework types according to the Atlas of Zeolite Structure Types. The MgAPSO-31 molecular sieve of U.S. Pat. No. 4,758,419, having a crystallographic free diameter of 5.4 Å, is especially preferred. MgAPSO sieves have a framework structure of $MgO_2^{-2}$, $AlO_2^{-}$, $PO_2^{+}$, and $SiO_2$ tetrahedral units having an empirical chemical composition on an anhydrous basis expressed by the formula:

$$mR:(Mg_wAl_xP_ySi_z)O_2$$

wherein "R" represents at least one organic templating agent present in the intracrystalline pore system; "m" represents the molar amount of "R" present per mole of $(Mg_wAl_xP_yS_z)O_2$ and has a value of zero to about 0.3; and "w", "x", "y" and "z" represent the mole fractions of elemental magnesium, aluminum, phosphorus and silicon, respectively, present as tetrahedral oxides. The mole fractions "w", "x", "y" and "z" are generally defined as being within the limiting compositional values or points as follows:

| | Mole Fraction | | |
|---|---|---|---|
| Point | x | y | (z + w) |
| A | 0.60 | 0.38 | 0.02 |
| B | 0.39 | 0.59 | 0.02 |
| C | 0.01 | 0.60 | 0.39 |
| D | 0.01 | 0.01 | 0.98 |
| E | 0.60 | 0.01 | 0.39 |

The MgAPSO-31 molecular sieve preferably has a framework magnesium content of from about 0.003 to 0.035 mole fraction, consistent with the teachings of U.S. Pat. No. 5,240,891 which is incorporated herein by reference thereto.

The preferred zeolitic aluminosilicates of the second catalyst are selected from those which have a $Si:Al_2$ ratio greater than about 10, preferably greater than 20, and a pore diameter of about 5 to 8 Angstroms (Å). Specific examples of suitable zeolites are the MFI, MEL, EUO, FER, MFS, MTT, MTW, TON, MOR and FAU types of zeolites. Pentasil zeolites MFI, MEL, MTW and TON are preferred, and MFI-type zeolites, often designated ZSM-5, are especially preferred.

The preparation of the preferred MFI-type zeolites by crystallizing a mixture comprising an alumina source, a silica source and an alkali metal source is well known in the art. Conversion of an alkali-metal-form zeolite to the hydrogen form may be performed by treatment with an aqueous solution of a mineral acid. Alternatively, hydrogen ions can be incorporated into the pentasil by ion exchange with ammonium salts such as ammonium hydroxide or ammonium nitrate followed by calcination.

The non-zeolitic molecular sieve and the zeolitic aluminosilicate each preferably are composited with a binder for convenient formation of catalyst particles. The proportion of NZMS in the first catalyst is about 5 to 90 mass-%, preferably about 10 to 80 mass-%, the remainder other than metal and other components discussed herein being the binder component. The relative proportion of zeolite in the second catalyst may range from about 10 to about 99 mass-%, with about 20 to about 90 mass-% being preferred.

The binder should be porous, adsorptive support having a surface area of about 25 to about 500 m²/g, uniform in composition and relatively refractory to the conditions utilized in the hydrocarbon conversion process. By the term "uniform in composition," it is meant that the support is unlayered, has no concentration gradients of the species inherent to its composition, and is completely homogeneous in composition. Thus, if the support is a mixture of two or more refractory materials, the relative amounts of these materials will be constant and uniform throughout the entire support. It is intended to include within the scope of the present invention carrier materials which have traditionally been utilized in hydrocarbon conversion catalysts such as: (1) refractory inorganic oxides such as alumina, titania, zirconia, chromia, zinc oxide, magnesia, thoria, boria, silica-alumina, silica-magnesia, chromia-alumina, alumina-boria, silica-zirconia, etc.; (2) ceramics, porcelain, bauxite; (3) silica or silica gel, silicon carbide, clays and silicates including those synthetically prepared and naturally occurring, which may or may not be acid treated, for example attapulgite clay, diatomaceous earth, fuller's earth, kaolin, kieselguhr, etc.; (4) crystalline zeolitic aluminosilicates, either naturally occurring or synthetically prepared such as FAU, MEL, MFI, MOR, MTW (IUPAC Commission on Zeolite Nomenclature), in hydrogen form or in a form which has been exchanged with metal cations, (5) spinels such as $MgAl_2O_4$, $FeAl_2O_4$, $ZnAl_2O_4$, $CaAl_2O_4$, and other like compounds having the formula $MO-Al_2O_3$ where M is a metal having a valence of 2; and (6) combinations of materials from one or more of these groups.

A preferred refractory inorganic oxide for use in the present invention is alumina. Suitable alumina materials are the crystalline aluminas known as the gamma-, eta-, and theta-alumina, with gamma- or eta-alumina giving best results.

An alternative preferred binder is a form of amorphous silica. The preferred amorphous silica is a synthetic, white, amorphous silica (silicon dioxide) powder which is classed as wet-process, hydrated silica. This type of silica is produced by a chemical reaction in a water solution, from which it is precipitated as ultra-fine, spherical particles. It is preferred that the BET surface area of the silica is in the range from about 120 to 160 $m^2/g$. A low content of sulfate salts is desired, preferably less than 0.3 wt. %. It is especially preferred that the amorphous silica binder be nonacidic, e.g., that the pH of a 5% water suspension be neutral or basic (pH about 7 or above).

A preferred shape for the catalyst composite is an extrudate. The well-known extrusion method initially involves mixing of the non-zeolitic molecular sieve, either before or after adding metallic components, with the binder and a suitable peptizing agent to form a homogeneous dough or thick paste having the correct moisture content to allow for the formation of extrudates with acceptable integrity to withstand direct calcination. Extrudability is determined from an analysis of the moisture content of the dough, with a moisture content in the range of from 30 to 50 wt. % being preferred. The dough then is extruded through a die pierced with multiple holes and the spaghetti-shaped extrudate is cut to form particles in accordance with techniques well known in the art. A multitude of different extrudate shapes are possible, including, but not limited to, cylinders, cloverleaf, dumbbell and symmetrical and asymmetrical polylobates. It is also within the scope of this invention that the extrudates may be further shaped to any desired form, such as spheres, by marumerization or any other means known in the art.

A favored alternative shape of the composite is a sphere continuously manufactured by the well-known oil drop method. Preparation of alumina-bound spheres generally involves dropping a mixture of molecular sieve, alumina sol, and gelling agent into an oil bath maintained at elevated temperatures. Alternatively, gelation of a silica hydrosol may be effected using the oil-drop method. One method of gelling this mixture involves combining a gelling agent with the mixture and then dispersing the resultant combined mixture into an oil bath or tower which has been heated to elevated temperatures such that gelation occurs with the formation of spheroidal particles. The gelling agents which may be used in this process are hexamethylene tetraamine, urea or mixtures thereof. The gelling agents release ammonia at the elevated temperatures which sets or converts the hydrosol spheres into hydrogel spheres. The spheres are then continuously withdrawn from the oil bath and typically subjected to specific aging treatments in oil and an ammoniacal solution to further improve their physical characteristics.

The resulting composites then preferably are washed and dried at a relatively low temperature of about 50–200° C. and subjected to a calcination procedure at a temperature of about 450–700° C. for a period of about 1 to about 20 hours.

The second catalyst optimally is subjected to steaming to tailor its acid activity. The steaming may be effected at any stage of the zeolite treatment, but usually is carried out on the composite of zeolite binder prior to incorporation of the platinum-group metal. Steaming conditions comprise a water concentration of about 5 to 100 volume-%, pressure of from about 100 kPa to 2 MPa, and temperature of between about 600° and 1200° C.; the steaming temperature preferably between about 650° and 1000° C., more preferably at least about 750° C. and optionally may be about 775° C. or higher. In some cases, temperatures of about 800° to 850° C. or more may be employed. The steaming should be carried out for a period of at least one hour, and periods of 6 to 48 hours are preferred. Alternatively or in addition to the steaming, the composite may be washed with one or more of a solution of ammonium nitrate, a mineral acid, and/or water. The washing may be effected at any stage of the preparation, and two or more stages of washing may be employed.

A platinum-group metal, including one or more of platinum, palladium, rhodium, ruthenium, osmium, and iridium, is an essential component of each of the present catalyst composites. The preferred platinum-group metal is platinum. The relative platinum-group metal content of each of the first and second catalysts is a feature of the invention. The platinum-group metal generally comprises from about 0.1 to about 2 mass-% of the final first catalyst and from about 0 to 0.2 mass-% of the second catalyst, calculated on an elemental basis; the second catalyst preferably comprises from about 0.02 to 0.08 mass-%, and optionally less than about 0.06 mass-% of platinum-group metal on an elemental basis. The content of platinum-group metal of the second catalyst is no more than about 30% of the content of platinum-group metal in the first catalyst, preferably no more than about 20% of the content of platinum-group metal in the first catalyst, and optionally no more than about 10% of the content of platinum-group metal in the first catalyst.

The platinum-group metal component may exist within the final catalyst composite as a compound such as an oxide, sulfide, halide, oxysulfide, etc., or as an elemental metal or in combination with one or more other ingredients of the catalyst composite. It is believed that the best results are obtained when substantially all the platinum-group metal component exists in a reduced state The platinum-group metal component may be incorporated into the catalyst composite in any suitable manner. One method of preparing the catalyst involves the utilization of a water-soluble, decomposable compound of a platinum-group metal to impregnate the calcined sieve/binder composite.

Alternatively, a platinum-group metal compound may be added at the time of compositing the sieve component and binder. Complexes of platinum-group metals which may be employed in impregnating solutions, co-extruded with the sieve and binder, or added by other known methods include chloroplatinic acid, chloropalladic acid, ammonium chloroplatinate, bromoplatinic acid, platinum trichloride, platinum tetrachloride hydrate, platinum dichlorocarbonyl dichloride, tetramine platinic chloride, dinitrodiaminoplatinum, sodium tetranitroplatinate (II), palladium chloride, palladium nitrate, palladium sulfate, diamminepalladium (II) hydroxide, tetramminepalladium (II) chloride, and the like. Preferably the platinum-group metal component is concentrated on the binder component of the catalyst by any method known in the art. One method of effecting this preferred metal distribution is by compositing the metal component with the binder prior to co-extruding the sieve and binder. The platinum-group metal component preferably is in higher concentration on the catalyst binder than on the SM-3 sieve component; more preferably about 60% or more, and most preferably at least about 80% of the platinum component is on the binder.

It is within the scope of the present invention that the present catalyst composites may contain other metal components known to modify the effect of the platinum-group metal component. Such metal modifiers may include rhenium, tin, germanium, lead, cobalt, nickel, indium, gallium, zinc, uranium, dysprosium, thallium, and mixtures thereof. Catalytically effective amounts of such metal modifiers may be incorporated into the catalyst by any means known in the art to effect a homogeneous or stratified distribution.

The catalyst of the present invention may contain a halogen component, comprising either fluorine, chlorine, bromine or iodine or mixtures thereof, with chlorine being preferred. Preferably, however, the catalyst contains no added halogen other than that associated with other catalyst components.

The catalyst composite is dried at a temperature of from about 100° to about 320° C. for a period of from about 2 to about 24 or more hours and, usually, calcined at a temperature of from 400° to about 650° C. in an air atmosphere for a period of from about 0.1 to about 10 hours until the metallic compounds present are converted substantially to the oxide form. If desired, the optional halogen component may be adjusted by including a halogen or halogen-containing compound in the air atmosphere.

The resultant calcined composites optimally are subjected to a substantially water-free reduction step to insure a uniform and finely divided dispersion of the optional metallic components. The reduction optionally may be effected in the process equipment of the present invention. Substantially pure and dry hydrogen (i.e., less than 20 vol. ppm $H_2O$) preferably is used as the reducing agent in this step. The reducing agent contacts the catalyst at conditions, including a temperature of from about 200° to about 650° C. and for a period of from about 0.5 to about 10 hours, effective to reduce substantially all of the Group VIII metal component to the metallic state. In some cases the resulting reduced catalyst composite may also be beneficially subjected to presulfiding by a method known in the art to incorporate in the catalyst composite from about 0.05 to about 1.0 mass-% sulfur calculated on an elemental basis.

EXAMPLES

The following examples are presented only to illustrate certain specific embodiments of the invention, and should not be construed to limit the scope of the invention as set forth in the claims. There are many possible other variations, as those of ordinary skill in the art will recognize, within the spirit of the invention.

Example I

Samples of the first catalyst comprising a non-zeolitic molecular sieve were prepared for comparative pilot-plant testing.

A catalyst containing MgAPSO-31 was prepared in accordance with the teachings of U.S. Pat. No. 5,240,891. $Al_2O_3$ as pseudoboehmite (Versal 250) was added into $H_3PO_4$ and water on a gradual basis and blended until a homogeneous mixture was observed. Magnesium acetate was dissolved in a portion of the water and then was added followed by addition of LUDOX-LS. The combined mixture was blended until a homogeneous mixture was observed. The organic templating agent and $AlPO_4$-31 seed were added to this mixture and blended until a homogeneous mixture was observed. The resulting mixture was heated to about 200° C. to effect crystallization at autogenous pressure. The products were removed from the reaction vessel and centrifuged to recover solids which were washed, dried and calcined at about 650° C. The resulting MgAPSO sieve was extruded with alumina in a 50/50 mass ratio, impregnated to effect a platinum content of 0.27 mass-%, calcined and reduced to yield Catalyst A.

A sample of a first catalyst comprising SM-3 silicoaluminophosphate was prepared for testing as isomerization catalysts in the process of the invention. The SM-3 was prepared according to the teachings of U.S. Pat. No. 4,943,424 (Miller) and had characteristics as disclosed in the '424 patent. The SM-3 SAPO-11 sieve was composited with alumina in an 85/15 mass ratio, impregnated to effect a platinum content of about 0.28 mass-%, calcined and reduced. This catalyst was designated as Catalyst B.

Example II

A sample of the second catalyst comprising a zeolitic aluminosilicate, in the form of an aluminum-phosphate-bound MFI, was prepared for pilot-plant testing. A first solution was prepared by adding phosphoric acid to an aqueous solution of hexamethylenetetraamine (HMT) in an amount to yield a phosphorus content of the finished catalyst equal to about 11 mass-%. A second solution was prepared by adding an ammonia-exchanged MFI-type zeolite having an $Si/Al_2$ ratio of about 39 to enough alumina sol, prepared by digesting metallic aluminum in hydrochloric acid, to yield a zeolite content in the finished catalyst equal to about 67 mass-%. These two solutions were commingled to achieve a homogeneous admixture of HMT, phosphorus, alumina sol, and zeolite. This admixture was dispersed as droplets into an oil bath maintained at about 93° C. The droplets remained in the oil bath until they set and formed hydrogel spheres having a diameter of about 1.6 mm. The spheres were removed from the oil bath, water washed, air dried, and calcined at a temperature of about 550° C. The calcined spheres then were subjected to steaming at a temperature of about 660° C. in an atmosphere of 40% steam in air.

The steamed spheres then were metal-impregnated using a solution of tetraamine platinum chloride. Upon completion of the impregnation, the catalyst was dried, oxidized, and reduced to yield a catalyst containing about 0.04 mass-% platinum. This isomerization catalyst was designated as Catalyst X.

Example III

Catalyst A was evaluated as a control not of the invention for isomerization of $C_8$ aromatics using a pilot-plant flow reactor processing a non-equilibrium $C_8$ aromatic feed having the following composition in mass-%:

| | |
|---|---|
| toluene + benzene | 1.53 |
| $C_7$ – nonaromatics | 0.07 |
| ethylbenzene | 18.46 |
| para-xylene | 0.91 |
| meta-xylene | 54.46 |
| ortho-xylene | 19.31 |
| $C_8$ nonaromatics | 4.58 |
| $C_9$ + aromatics | 0.01 |
| $C_9$ + nonaromatics | 0.67 |

This feed was contacted with Catalyst A at a liquid hourly space velocity of 2.5, and a hydrogen/hydrocarbon mole ratio of 4. Reactor temperature was adjusted to effect a favorable conversion level.

Example IV

The catalyst system of the invention was evaluated in pilot-plant tests in comparison to controls not of the invention for isomerization of a $C_8$ aromatics feedstock. The control catalysts not of the invention were Catalyst B and a stacked bed of Catalyst B in front of Catalyst A in a 50/50 mass ratio. The catalyst system of the invention was a stacked bed of Catalyst A in front of Catalyst X in a 50/50 mass ratio.

The catalysts were evaluated using a pilot-plant flow reactor processing a non-equilibrium $C_8$ aromatic feed having the following composition in mass-%:

| | |
|---|---|
| toluene + benzene | 0.78 |
| $C_7$ – nonaromatics | 0.29 |
| ethylbenzene | 16.35 |
| para-xylene | 0.22 |
| meta-xylene | 49.00 |
| ortho-xylene | 23.23 |
| $C_8$ nonaromatics | 9.49 |
| $C_9$ + aromatics | 0.04 |
| $C_9$ + nonaromatics | 0.60 |

This feed was contacted with 150 cc of catalyst at liquid hourly space velocities of 2.7, 2.5 and 1.7, respectively for catalysts B, B/A and A/X, and a hydrogen/hydrocarbon mole ratio of about 4. Reactor temperature was adjusted to effect a favorable conversion level. Conversion is expressed as the disappearance per pass of ethylbenzene. $C_8$ aromatic loss is primarily to benzene and toluene, with smaller amounts of light gases being produced. Results were as follows, including the Example III results:

| | Controls | | | Invention |
|---|---|---|---|---|
| Catalyst | A | B | B/A | A/X |
| Temperature ° C. | 386 | 369 | 381 | 378 |
| Ethylbenzene conversion, % | 22.7 | 25.5 | 23.9 | 37.6 |
| Xylene gain, mass-% | 1.28 | 5.26 | 3.92 | 3.99 |
| p-xylene/xylenes, mole-% | 21.9 | 21.4 | 22.1 | 22.6 |

The catalyst system of the invention was particularly effective in converting ethylbenzene and achieving a high proportion of para-xylene in total xylenes. These results are shown in the FIGURE for the three pilot-plant runs on the Example IV feedstock.

We claim:

1. A catalyst system comprising a combination of:
   (a) a first catalyst comprising from about 0.1 to 2 mass-% of at least one platinum-group metal component, about 10 to 90 mass-% of at least one non-zeolitic molecular sieve, and an inorganic-oxide binder; and,
   (b) a second catalyst comprising from about 0.02 to 0.08 mass-% of at least one platinum-group metal component, from about 10 to 99 mass-% of at least one zeolitic aluminosilicate, and an inorganic-oxide binder, wherein the content of platinum-group metal is no more than about 30% of the content of platinum-group metal in the first catalyst.

2. The catalyst system of claim 1 wherein the content of platinum-group metal in the second catalyst is no more than about 20% of the content of platinum-group metal in the first catalyst.

3. The catalyst system of claim 2 wherein the content of platinum-group metal in the second catalyst is no more than about 10% of the content of platinum-group metal in the first catalyst.

4. The catalyst system of claim 1 wherein the second catalyst comprises less than about 0.06 mass-% of platinum-group metal.

5. The catalyst system of claim 1 wherein the non-zeolitic molecular sieve of the first catalyst comprises a crystalline SAPO-11 molecular sieve.

6. The catalyst system of claim 5 wherein the crystalline SAPO-11 molecular sieve is an SM-3 molecular sieve.

7. The catalyst system of claim 1 wherein the non-zeolitic molecular sieve of the first catalyst comprises a MgAPSO-31 molecular sieve.

8. The catalyst system of claim 7 wherein the MgAPSO-31 molecular sieve has a framework magnesium content of from about 0.03 to 0.035 mole fraction.

9. The catalyst system of claim 1 wherein a first:second catalyst mass ratio is from about 1:20 to 50:1.

10. The catalyst system of claim 1 comprising a physical mixture of first particles comprising the non-zeolitic molecular sieve and second particles comprising the zeolitic aluminosilicate.

* * * * *